United States Patent [19]
Martin et al.

[11] Patent Number: 5,368,594
[45] Date of Patent: Nov. 29, 1994

[54] VERTEBRAL OSTEOSYNTHESIS DEVICE

[75] Inventors: Jean-Jacques Martin; Jean-Philippe Lescuyer, both of Bourg en Bresse; René Cartoux, Gordes; Jean-Jacques Lalain, Fontaines Saint Martin; Frédéric Michel, Lyons; Jacques Samani, St Cyr Au Mont D'Or, all of France

[73] Assignee: Fixano S.A., Bourg en Bresse, France

[21] Appl. No.: 44,378

[22] Filed: Apr. 2, 1993

[51] Int. Cl.⁵ .................................................. A61F 5/01
[52] U.S. Cl. .................................... 606/61; 128/899; 623/17
[58] Field of Search ................ 128/897, 899; 606/60–75; 623/17; 602/5, 12, 18, 19, 20, 23, 32, 36

[56] References Cited

U.S. PATENT DOCUMENTS

| | | | |
|---|---|---|---|
| 4,950,269 | 8/1990 | Gaines, Jr. | 606/61 |
| 5,084,049 | 1/1992 | Asher et al. | 606/60 |
| 5,092,893 | 3/1992 | Smith | 606/60 |
| 5,176,680 | 1/1993 | Vignaud et al. | 606/60 |
| 5,217,497 | 6/1993 | Mehdian | 606/61 |

FOREIGN PATENT DOCUMENTS

| | | | |
|---|---|---|---|
| 0301489 | 2/1989 | European Pat. Off. | 623/17 |
| 0330881 | 9/1989 | European Pat. Off. | 623/17 |
| 0346521 | 12/1989 | European Pat. Off. . | |
| 0348272 | 12/1989 | European Pat. Off. | 623/17 |
| 0528706 | 2/1993 | European Pat. Off. | 606/61 |
| 2345363 | 7/1974 | Germany . | |
| 91/01691 | 2/1991 | WIPO . | |

Primary Examiner—Lee S. Cohen
Assistant Examiner—J. P. Lacyk
Attorney, Agent, or Firm—Oliff & Berridge

[57] ABSTRACT

A vertebral osteosynthesis device employs outside faces of lateral walls of each hooking element which are inclined toward each other such that they converge from the side opposite hooking elements designed to be attached to the bone, while a gripping element in the shape of a clamp has side arms with inside faces inclined at slopes that match those of outside faces of lateral walls. At least two gripping means are disposed beyond the lateral walls and are provided to move the gripping element such that the inside faces of its lateral arms abut the lateral walls, bringing them toward each other and sliding on them upon gripping, to bring the lateral walls closer together to lock each hooking element onto a support rod.

14 Claims, 2 Drawing Sheets

VERTEBRAL OSTEOSYNTHESIS DEVICE

BACKGROUND OF THE INVENTION

The present invention relates to a vertebral osteosynthesis device that can be used simply to brace a spine that requires it, for example following accidental fracture, or to straighten and brace a deviated spine, as in the case of scoliosis or kyphosis.

As is known, such a device can comprise two rigid and substantially parallel support rods disposed one on each side of the spinous processes of the vertebrae, on which bone-anchoring elements may be mounted. The bone anchoring elements can be constituted either by hooks designed to fit around the spinous processes or by screws designed to be supported by the pedicles of the vertebrae.

Implantation of a device of this kind requires precise shaping of the rods to adapt them to the curves in one or two planes of the spine, whether these are natural curves or curves resulting from kyphosis or scoliosis, and requires a perfect link to be achieved between the rods and the anchoring elements. The link must be capable of withstanding the repeated stresses over time to which the various elements are subjected by the patient's movements.

International patent application No. WO 91/01691 and European Patent Application No. 0,346,521 describe more specifically anchoring elements comprising, two lateral walls projecting from the side opposite their hooking elements, substantially parallel and flexible, delimiting between them a channel, the width of which is substantially equal to the diameter of the rods, and, a gripping element able to engage the lateral walls and bring them closer together during said engagement. The rods are introduced into the channels and then the gripping elements are put in place. The radial grip exerted on the rod by deformation of said walls and the substantial contact area between the rod and the walls ensure that the hooking elements remain integral with the rod.

The aforementioned shaping of the rods is not easy with these devices because, as long as the rod is not held between flexible legs, it is difficult to check that the shape conferred on the rods is correct or whether this shape must be reworked. Moreover, the strength over time of the anchoring element/rod linkage is uncertain because the attachment of the gripping elements depends on the flexure of the legs.

In addition, the gripping elements have the disadvantages of being difficult to set in place and tighten, and of not allowing the practitioner to be fully in control of the grip on the rod that they produce. The gripping action of the rod is made difficult by the deformation of the walls. Moreover, access to the gripping elements is somewhat limited and is problematical when the gripping elements are constituted by nuts that can be screwed to the ends of the walls because the possible play of the gripping wrench is particularly small in view of the size of the incision and the presence of various instruments.

Moreover, in certain cases it may be useful to achieve a grip that is just sufficient temporarily to immobilize the rods relative to the hooking elements but without locking them permanently together with a view, in particular, to subsequent verification of the curvature of the rods.

SUMMARY OF THE INVENTION

The goal of the present invention is to provide a vertebral osteosynthesis device which overcomes the foregoing disadvantages.

For this purpose, in the device of the aforementioned type, the distance between the inside faces of the lateral walls, near their upper ends, is slightly less than the diameter of the rods so that the rods can be held provisionally together by clipping. The outer faces of the lateral walls are inclined toward each other, so that they converge on the side opposite the hooking element which is to be attached to the bone, the gripping element being in the shape of a clamp, side arms of which have inside faces inclined at slopes that match those of the outside faces of the lateral walls, and comprising at least two gripping means disposed beyond the lateral walls, designed to displace said gripping element such that the inside faces of its side walls abut the lateral walls, bringing them toward each other by sliding on them when gripping is effected.

Thus, the invention allows easy provisional placement and withdrawal of the rods outside the anchoring elements so that the shapes of the rods can be evaluated and they can be reworked if necessary.

Moreover, the link provided by the invention is entirely sound and strong over time because the gripping means of the clamp on the heads of the screws or hooks do not rest on the flexible lateral legs. The latter, once the clamp is tightened, are perfectly maintained and can thus have the relative flexibility necessary to allow the aforesaid clipping prior to clamping.

The fact of providing several gripping means disposed laterally also allows the deformation of the lateral walls and hence the gripping exerted by them on the rod to be fully checked. The gripping precision thus obtained therefore allows just enough gripping to immobilize the rod relative to the hooking elements without locking it permanently in place so that the match of its shape with the curves of the spine can later be checked.

Overall, the invention allows the duration of surgery to be considerably reduced and hence the duration of the anesthesia the patient must undergo and the consumption of transfused blood products.

Advantageously, said gripping means are composed of two screws, the heads of which abut the outer face of the central part of the clamp and the bodies of which traverse parallel arms of the clamp. The screws are engaged in tapped bores provided in two projections located outside the lateral walls, on each hooking element.

The screws are thus fully accessible and easy to manipulate, particularly when their heads are of the hexagonal type.

According to one possibility, the central part of each lateral wall is machined or hollowed to allow the screws to pass through. Thus a considerable space saving is obtained for the hooking elements.

Preferably, two slots are provided in each hooking element in between the lateral walls, near their bases. These slots confer increased flexibility on the lateral walls, facilitating gripping. According to one preferred embodiment of the invention, these slots are provided radially relative to the rod.

In any event, the invention will be understood with the aid of the description hereinbelow with reference to the attached schematic drawing which represents, as a nonlimiting example, one preferred embodiment of a vertebral osteosynthesis device incorporating the invention.

DESCRIPTION OF PREFERRED EMBODIMENTS

Figure 4:
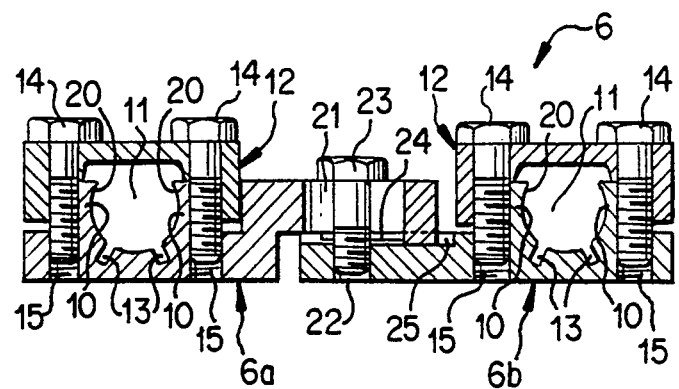
FIG. 4 is a section along line IV—IV in FIG. 1.
Figure 1:
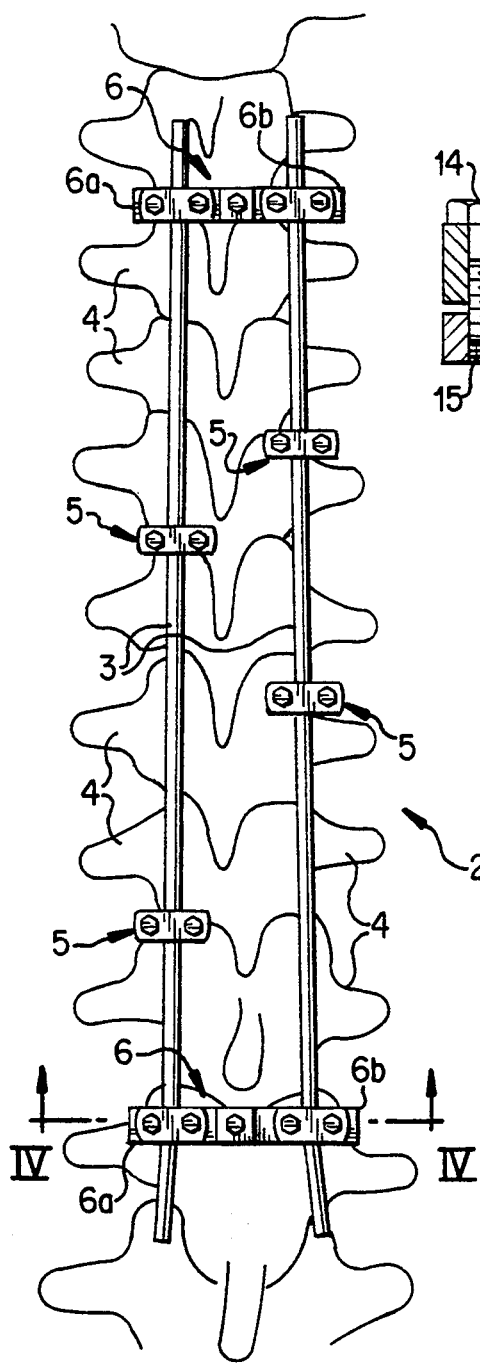
FIG. 1 is an elevational view of the device when mounted on a spine.
Figure 2:
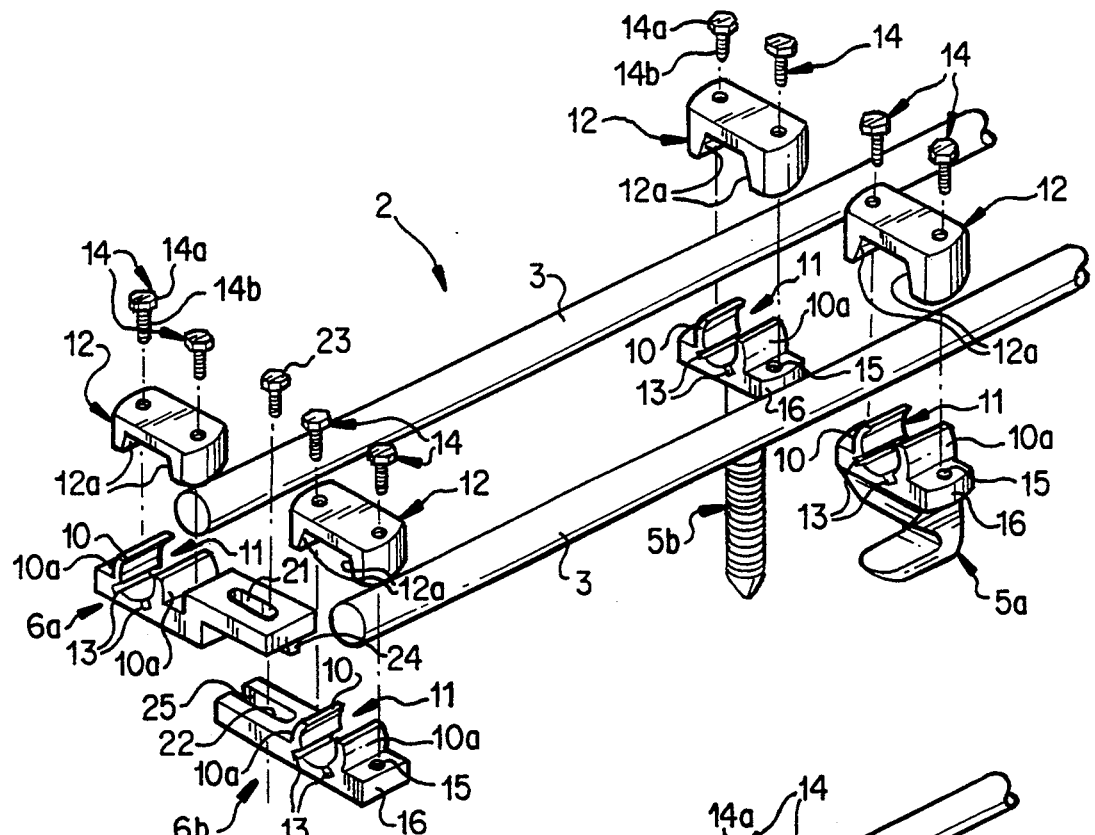
FIGS. 2 and 3 are partial views of the device, one in exploded perspective and one in mounted perspective.
Figure 3:
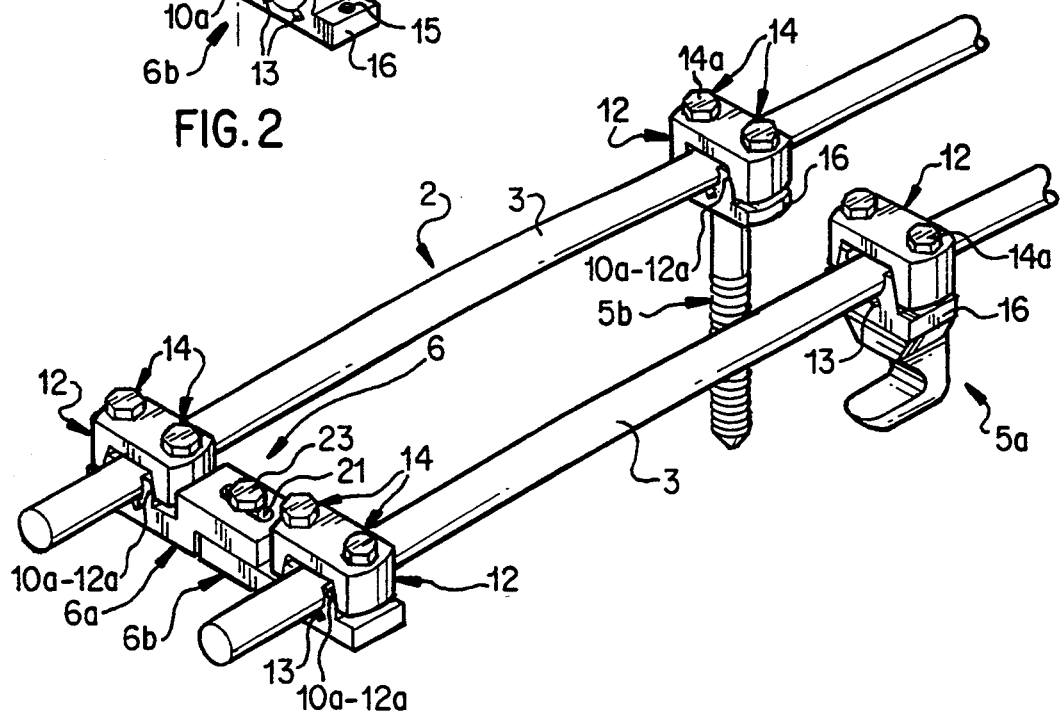

FIG. 1 shows a vertebral osteosynthesis device 2 comprising two rigid support rods 3 which are substantially parallel and disposed one on each side of the spinous processes of vertebrae 4. Preferably, the rods are cylindrical and have a substantially circular cross section. Bone-anchoring elements 5 can be mounted on rods 3, which elements may be constituted, as shown more particularly in FIGS. 2 and 3, either by hooks 5a designed to fit around the vertebral processes, or by screws 5b designed to be supported on the pedicles of vertebrae 4. Device 2 also comprises at least one transverse element 6 composed of two parts 6a and 6b joined together, as shown in FIGS. 2 to 4. Elements 6 are designed to connect rods 3 to each other.

As can be seen in FIGS. 2 to 4, each of hooking elements 5 or parts 6a or 6b comprises, on the one hand, two lateral walls 10 that project, as regards hooking elements 5, on the side opposite hooking elements 5a, 5b, which they comprise, these walls being substantially parallel and flexible and delimiting between them a channel 11 which matches the diameter of rods 3, and, on the other hand, a gripping element 12 which can be engaged on the sides of walls 10.

As can be seen clearly in the figures, outside faces 10a of lateral walls 10 are inclined toward each other so that they converge, as regards hooking elements 5, on the side opposite hooking elements 5a or 5b and, as regards parts 6a and 6b, on the side opposite vertebrae 4, when device 2 is set in place on the spine.

Two slots 13 are provided in each hooking element 5 and in each part 6a or 6b between lateral walls 10, near their bases. The slots are preferably arranged to extend radially of a rod 3 fully received in channel 11.

Gripping element 12 is in the shape of a clamp with side arms have inside faces 12a inclined at slopes that match those of outside faces 10a of lateral walls 10.

In addition, each hooking element 5 or part 6a, 6b has two screws 14 having heads 14a, which are hexagonal in shape, and rest on the outside face of the central part of the clamp formed by gripping element 12. Screw bodies 14b, which traverse the parallel arms of the gripping element, engage tapped bores 15 provided in two projections 16 located outside the lateral walls 10 of each hooking element 5 or each part 6a, 6b.

FIG. 4 shows in particular that the central part of lateral walls 10 can be machined or even hollowed starting from face 10a to allow passage of screws 14 and thus achieve a substantial space saving.

FIG. 4 also shows that the inside faces of lateral walls 10 include, in the vicinity of their upper ends, facing projections 20, the distance separating the projections 20 on each pair of lateral walls 10 being slightly less than the diameter of rods 3. Lateral walls 10 of hooking elements 5 are also provided with such projections.

In practice, the shaping of rods 3 according to the curvature or curvatures of the spine is adjusted by clipping rods 3 in channels 11, which is made possible by projections 20 or simply by the distance between the inside faces of lateral walls 10, at their upper ends, being less than the diameter of rods 3.

Faces 12a of gripping elements 12 are designed to abut faces 10a of lateral walls 10 and bring them closer together when screws 14 are tightened. Screws 14 are easy to manipulate and their lateral disposition on each hooking element 5 or part 6a or 6b allows the deformation of lateral walls 10 to be fully controlled, and hence the grip exerted by them on rods 3. The gripping precision thus obtained allows a grip that is just sufficient to immobilize rods 3 relative to hooking elements 5 temporarily before permanent locking, for a later check that the rods match the curves of the spine.

Moreover, clamps 12 are attached by means of screws 14, namely independently of the flexibility of lateral walls 10, so that the link between rods 3 and anchoring elements 5 obtained is quite sound and enduring over time.

Transverse elements 6, because they are composed of two parts 6a, 6b, joined together, can be installed any point on rods 3, particularly between two pairs of hooking elements 5 that have been previously set in place, if necessary. Each of parts 6a and 6b is fitted around one of rods 3, then parts 6a and 6b are joined together. FIGS. 2 to 4 show that part 6a has an oblong hole 21 provided along its lengthwise axis and that part 6b has a tapped bore 22, a screw 23 being provided to pass through said hole 21 and be engaged in said bore 22, then tightened. The lengths of elements 6 are thus adjustable so that it is unnecessary to have available a whole set of elements with different lengths. Part 6a also has a tongue 24 while part 6b has a matching groove 25, such that parts 6a, 6b can be guided translationally with respect to each other. Hence any angling of rods 3 is prevented.

We claim:

1. A vertebral osteosynthesis device for affixation to vertebrae, comprising:

two rigid support rods adapted to be disposed substantially parallel, one on each side of spineous processes of the vertebrae;

a plurality of bone anchoring elements, each bone anchoring element having one of a hook element adapted to fit around a vertebral process and a screw element adapted to be screwed into a vertebral pedicle and each bone anchoring element having two lateral walls extending in a direction opposite said hook and screw elements, said lateral walls being substantially parallel and flexible and having inside and outside faces, and upper and lower ends, said outside faces being inclined toward each other at the upper ends, said lateral walls delimiting between them a channel matching a transverse dimension of said support rods, the distance separating said lateral walls at the upper ends thereof being slightly less than the transverse dimension of said support rods whereby said bone anchoring elements may be provisionally attached to said support rods by clipping said bone anchoring elements to said support rods;

a plurality of gripping elements, each gripping element being associated with a bone anchoring element and having two opposed side arms, the side arms having inside faces and outside faces, the inside faces being inclined at a slope matching the outside faces of said lateral walls and adapted to engage the outside faces of said lateral walls and to bring said lateral walls closer together during engagement of said lateral walls; and a plurality of gripping means for attaching said gripping elements to said bone anchoring elements, each of said gripping means passing through a side arm of a gripping element and threadably engaging a bone anchoring element and displacing said gripping element whereby the inside faces of said gripping elements engage and slide on said outside faces of said lateral walls of said bone anchoring elements to bring said lateral walls closer together.

2. The device of claim 1, wherein said bone anchoring elements further comprise two extensions adapted to threadably engage said gripping means and wherein each of said gripping means comprises a screw having a head adapted to rest on a portion of one of said gripping elements and having a body adapted to pass through one of said side arms of said gripping elements.

3. The device of claim 1, wherein portions of said lateral walls are removed and said gripping means pass through the portion removed.

4. The device of claim 1, wherein slots are provided in said lateral walls to increase the flexibility of said lateral walls.

5. The device of claim 4, wherein said slots extend into said bone anchoring elements in a radial direction of said channel.

6. The device of claim 1, further comprising two projections, each of said projections located at an upper end of an inner face of a lateral wall, whereby the two projections of a bone anchoring element are located opposite each other.

7. The device of claim 1, further comprising a transverse element, said transverse element having a first part and a second part, each of said first and second parts having two lateral walls, a gripping element, and gripping means for securing said gripping element to said first and second parts.

8. The device of claim 7, wherein said transverse element further comprises screw means for holding said first and second parts together, and wherein said first part includes an oblong hole, and wherein said screw means passes through said oblong hole.

9. The device of claim 7, wherein one of said first and second parts includes a groove, and the other of said first and second parts includes a tongue adapted to be received in said groove.

10. The device of claim 1, wherein said support rods have a substantially circular cross section having a diameter slightly greater than the distance separating the upper ends of said lateral walls.

11. An osteosynthesis device comprising:
at least one support rod for supporting vertebrae of a spine;
at least one bone-anchoring element for anchoring the support rod to the spine, the bone anchoring element including a base;
a hooking element for affixing the bone-anchoring element on vertebrae of the spine extending from the base, a pair of opposed lateral walls projecting from the base in a direction away from the hooking element, the lateral walls having opposed inside faces, the inside faces defining a channel formed between the lateral walls for receiving the support rod, each lateral wall having an outside surface, the outside surface of one lateral wall converging toward the outside surface of the opposite lateral wall; said base having portions extending transversely beyond each lateral wall;
a gripping element having a pair of opposed side arms, each side arm including an engaging surface for engaging the outside surface of one of the lateral walls, each engaging surface being inclined in a direction to urge the lateral walls toward each other in response to movement of the gripping element toward the base; and
a pair of fasteners for mounting the gripping element on the base and moving the gripping element toward the base, each fastener being located to engage an associated one of the portions of the base extending transversely beyond each lateral wall.

12. The osteosynthesis device of claim 11, wherein upper opposed ends of said inside faces are spaced apart a distance slightly less than a transverse dimension of the rod before said ends are drawn toward each other by the gripping element.

13. The osteosynthesis device of claim 11, wherein a groove is formed in the inside surface of each lateral wall and adjacent the base.

14. The osteosynthesis device of claim 13, wherein the support rod has a circular cross section and said groove extends radially with respect to a support rod received in the channel.

* * * * *